(12) United States Patent
Mir-Shekari et al.

(10) Patent No.: US 6,416,997 B1
(45) Date of Patent: Jul. 9, 2002

(54) RECEPTOR-BINDING POCKET MUTANTS OF INFLUENZA A VIRUS HEMAGGLUTININ FOR USE IN TARGETED GENE DELIVERY

(75) Inventors: Yasamin Mir-Shekari, London (GB); Paul Bates, Swarthmore, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/525,392

(22) Filed: Mar. 15, 2000

Related U.S. Application Data

(63) Continuation of application No. PCT/US98/19552, filed on Sep. 17, 1998.
(60) Provisional application No. 60/059,239, filed on Sep. 18, 1997.

(51) Int. Cl.[7] .......................... C12N 15/00; C12Q 1/70; C12P 21/04; C07H 21/04; A61K 39/12
(52) U.S. Cl. ......................... 435/320.1; 435/5; 435/6; 435/7.2; 435/69.7; 435/339; 536/23.72; 424/199.1
(58) Field of Search ....................... 435/5, 6, 7.2, 69.7, 435/339, 320.1; 536/23.72; 424/199.1

(56) References Cited

PUBLICATIONS

Bron et al., 1993, Methods in Enzymology 220:313–341.
Connor et al., 1995, Virology 206:935–944.
Kasahara et al., 1994, Science 226:1373–1376.
Naldini et al., 1996, Science 272:263–267.
Nobusawa and Nakajima, 1988, Virology 167:8–14.
Rogers et al., 1983, Nature 304:76–79.
Rong and Bates, 1995, J. Virol. 69:4847–4853.
Soneoka et al., 1995, Nucl. Acid. Res. 23:628–633.
Steinhauer et al., 1996, Proc. Natl. Acad. Sci. USA 93:12873–12878.
Verhoeyen et al., 1980, Nature 286:771–776.
Weis et al., 1988, Nature 333:426–431.
Wiley 1985, In: *Fields' Virology*, pp. 45–52, Raven Press, New York.
Wilson et al., 1981, Nature 289:366–373.

*Primary Examiner*—Hankyel T. Park
(74) *Attorney, Agent, or Firm*—Morgan, Lewis & Bockius LLP

(57) ABSTRACT

The invention relates to a lipid containing vector capable of fusing to a cell membrane and delivering a compounds contained therein to a cell, and methods of use thereof.

30 Claims, 12 Drawing Sheets

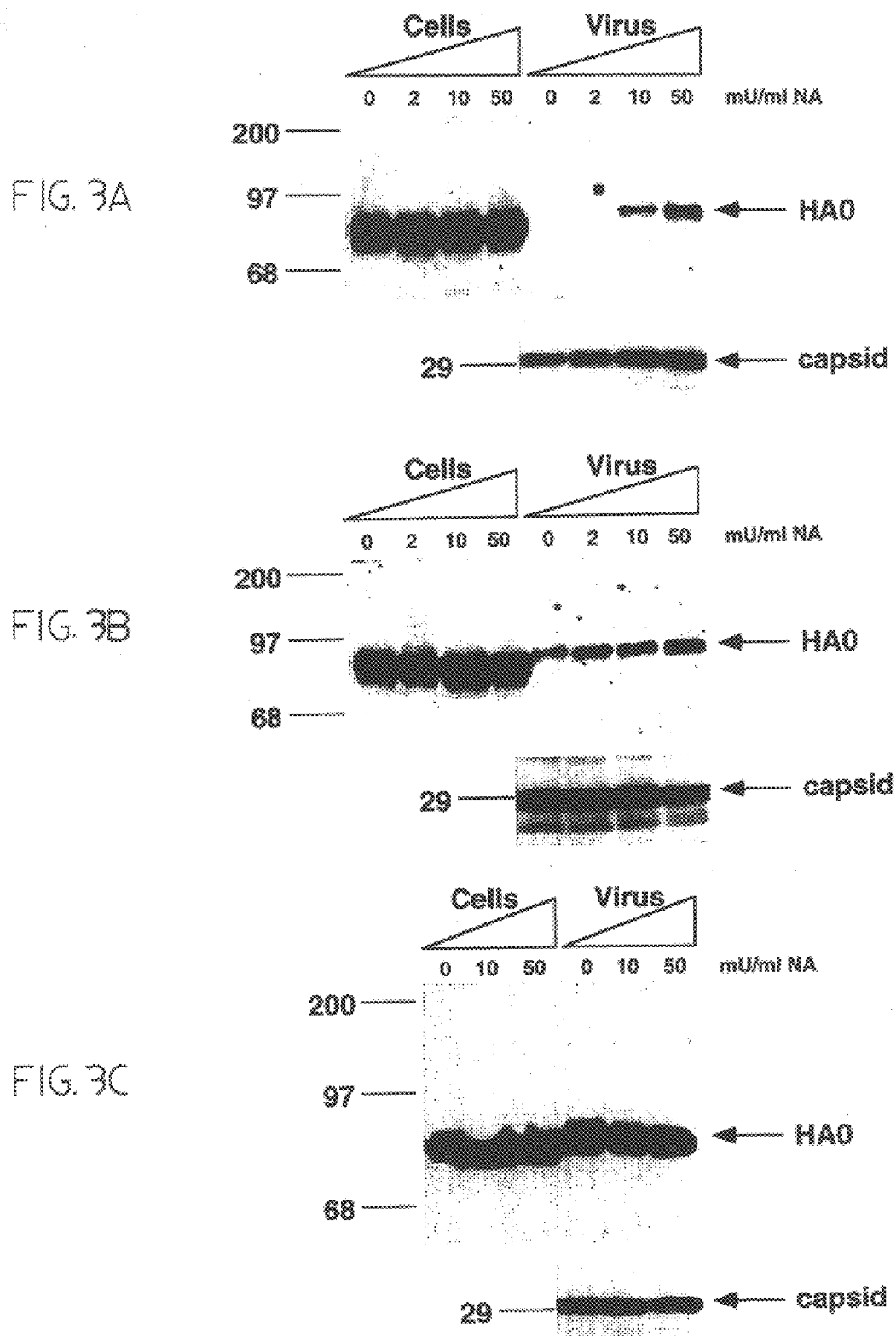

pH 7.0          pH 4.8
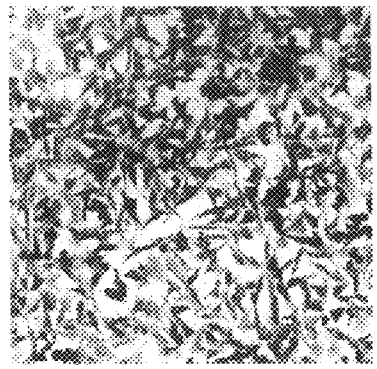
FIG.5A-1
− Trypsin
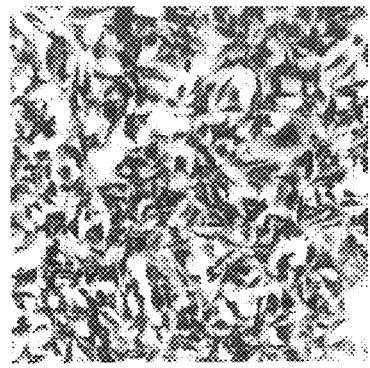
FIG.5A-2
+ Trypsin
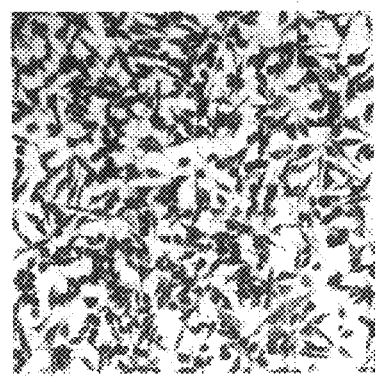
FIG.5A-3
FIG.5A-4

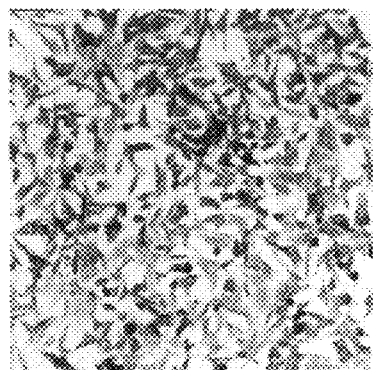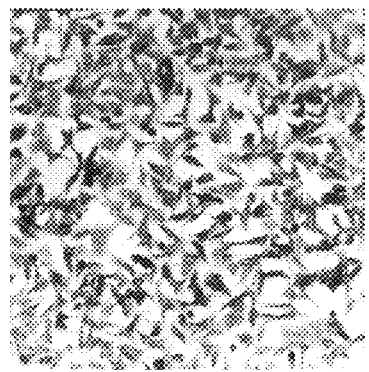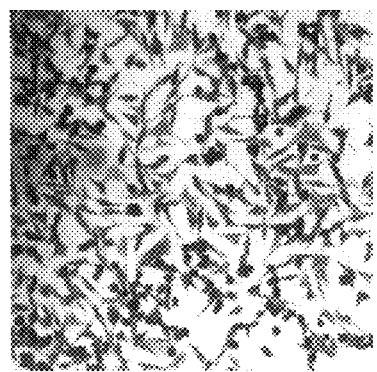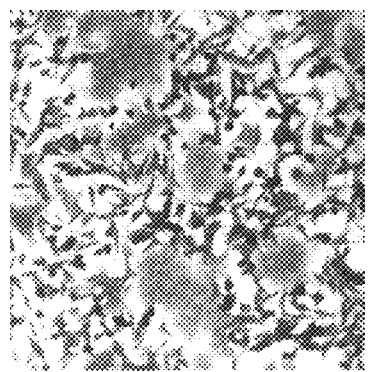

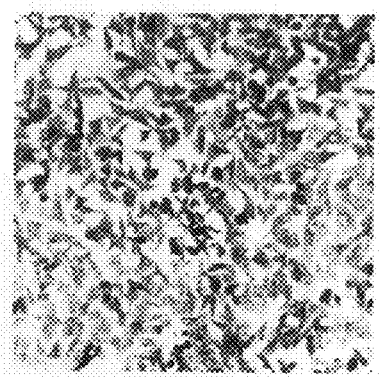
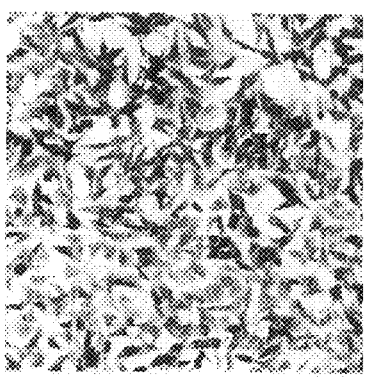
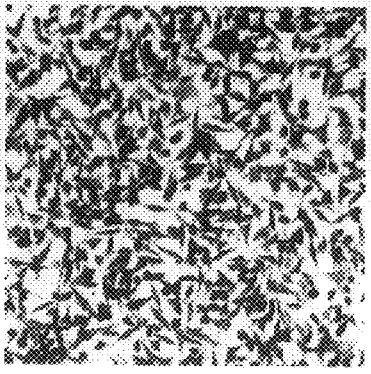
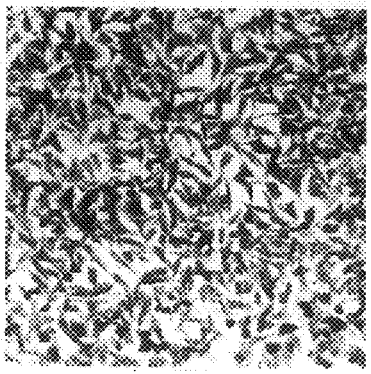
FIG.5C-1 −Trypsin pH 7.0
FIG.5C-3 pH 4.8
FIG.5C-2 +Trypsin
FIG.5C-4

Fig. 9

Bar chart: TITER (IU/ml) vs VIRUS
- MLV(-): ~0
- MLV(HA): ~500
- MLV(HA[T155S,L226V]): ~0
- MLV(HA[T155S,L226V,H17Q]): ~0
- MLV(HA[T155S,L226V,D112G]): ~0
- MLV(TvaEGF): ~2000
- MLV(HA/TvaEGF): ~4500
- MLV(HA[T155S,L226V]/TvaEGF): ~8500
- MLV(HA[T155S,L226V,H17Q]/TvaEGF): ~40000
- MLV(HA[T155S,L226V,D112G]/TvaEGF): ~57000

RECEPTOR-BINDING POCKET MUTANTS OF INFLUENZA A VIRUS HEMAGGLUTININ FOR USE IN TARGETED GENE DELIVERY

This is a continuation of PCT/US98/19552 filed Sep. 17, 1998 and claims the benefit of No. 60/059,239 filed Sep. 18, 1997.

FIELD OF THE INVENTION

The field of the invention is gene therapy, particularly the use of enveloped vectors for gene delivery.

BACKGROUND OF THE INVENTION

Infection of a host cell by an enveloped virus is initiated by binding of at least one viral envelope protein to a cognate virus receptor molecule on the cell surface. The viral envelope protein not only binds to the receptor but also catalyzes fusion of the viral envelope and the host cell membrane. The presence or absence on a cell of a cognate virus receptor molecule is a primary determinant of the host range and the tissue tropism of any given virus.

Hemagglutinin (HA) is the major surface protein of influenza A virus, and it is perhaps the best-characterized membrane protein. HA is synthesized as a single polypeptide precursor, HO, which is proteolytically cleaved into two subunits HA1 and HA2, either in the late Golgi or extracellularly, depending on the nature of the cleavage site as reviewed in Klenk and Garten (Trends Microbiol. 2:39–43). HA initiates infection by binding a sialic acid-containing virus receptor molecule on the surface of a target cell (Paulson, 1985, In: *The Receptors*, Vol. 2, pp.131–219, Conn, ed., Academic Press, Orlando, Fla.). Detailed structural studies further revealed that there is a region in the HA1 subunit that binds sialic acid which region has been named the receptor binding pocket (RBP) (Weis et al., 1988, 333:426–431). The RBP comprises several highly conserved amino acid residues, all of which are involved in the hydrogen-bond network which defines the RBP topography, and some of which are directly involved in sialic acid binding (Weis et al., supra).

After receptor-mediated endocytosis into an endosomal compartment, HA undergoes a series low-pH-induced conformational changes to a fusogenic form which mediates fusion of the viral envelope with the host cell membrane, resulting in introduction of the core of the virus into the host cell.

Assumption of the membrane-fusion-promoting conformation by HA is dependent on low pH, and is not dependent on sialic acid-containing-receptor binding since low pH alone in the absence of sialic acid binding is able to render HA fusogenic. Thus, if the virus and host cell membranes are in close enough proximity, low pH is sufficient to trigger fusion. Indeed, in the presence of streptavidin, virosomes comprising HA and biotinylated lipids fuse in a low-pH dependent manner with liposomes which also comprise biotinylated lipids, but which do not comprise sialic acid (Schoen et al., 1996, FEBS Letters 390:315–318). Therefore, the sialic acid receptor binding most likely ensures that the two desired membranes are sufficiently close at the time the pH is lowered to enable fusion. Indeed, the physical proximity of the two membranes at the time of pH-induced HA conformational changes is crucial for successful membrane fusion, since for most HA types, low pH treatment in the absence of a target membrane results in irreversible fusion inactivation of HA.

The amino acid sequence and detailed structural information for HA have been reported (Wilson et al., 1981, Nature 289:366–373; Weis et al., 1988, Nature 333:426–431), as has been the sequence of the gene encoding HA (Verhoeyen et al., 1980, Nature 286:771–776). The sequence of this gene encoding HA is available in the GenBank (Accession No. V01085). The sequence of the influenza virus A strain X-31 containing the A/Aicha/2/6B (H3N2) gene is set forth in the GenBank at Accession No. J02090. Strain X-31 is the strain used to determine the crystal structure of HA, and strain X-31 was used in the experiments disclosed herein.

Although an enveloped virus preferentially incorporates its own viral envelope proteins into its envelope during viral packaging, the tropism of a number of enveloped viruses may be altered by the acquisition an envelope glycoprotein encoded by a different virus having a different tropism. The exogenous envelope protein is acquired during virus assembly by a process denoted phenotypic mixing or pseudotyping. Pseudotyped viruses can be formed by co-infection of a cell by two different enveloped viruses or they can be generated experimentally by expressing a nucleic acid encoding an exogenous viral envelope protein in a cell producing an enveloped virus. Pseudotype formation in vivo has been postulated to provide a mechanism whereby the pathologic potential of an enveloped virus can be modified by co-infection of host cells with a viruses encoding differing envelope proteins.

The production of a pseudotyped virus having an envelope fusion protein comprising a portion of a viral envelope protein fused with a portion of an exogenous protein recognized by a particular cell surface receptor was first reported by Kasahara et al. (1994, Science 226:1373–1376). Kasahara et al., replaced the amino-terminus of the ecotropic Murine Leukemia Virus (MLV) envelope protein Eco-Env with the polypeptide hormone erythropoietin (EPO) to form the fusion protein Eco-Env-EPO. Kasahara et al., demonstrated specific targeting of virions comprising Eco-Env-EPO to cells expressing the EPO cell surface receptor in tissue culture.

However, even in the presence of the wild type virus envelope, the infectious titers of the EPO-encoding pseudotyped MLV and of other similar retroviral vectors are generally too low to be useful in a clinical setting. In addition, alteration of viral envelope proteins for the purpose of altering the tropism of the virion has invariably affected the fusogenic capacity of the altered virion envelope protein to induce fusion of the virion envelope with the target cell membrane.

Thus, a significant unmet need remains for the development of an agent which can be incorporated into the envelope of a virion and which is capable of inducing fusion of the virion envelope with the membrane of a desired target cell, wherein the fusion-inducing capacity of the agent is substantially independent of the tropism of the virion. The present invention meets this need.

SUMMARY OF THE INVENTION

The invention relates to a lipid-containing vector capable of fusing to a cell membrane. The vector comprises a mutant hemagglutinin, wherein the hemagglutinin comprises a mutation in the receptor binding pocket of the hemagglutinin, wherein the mutation substantially abrogates binding of the hemagglutinin to a sialic acid containing receptor, and further wherein the mutation does not affect the fusogenic capacity of the hemagglutinin.

In one aspect, the hemagglutinin is an influenza A virus hemagglutinin.

In another aspect, the mutant hemagglutinin comprises a mutation in at least one amino acid in the receptor-binding pocket of the influenza A virus hemagglutinin.

In a preferred embodiment, the amino acid sequence of the mutant hemagglutinin differs from the amino acid sequence of wild type influenza A virus hemagglutinin in at least one of histidine-17, aspartic acid-112, threonine-115, glutamine-190, and leucine-226.

In another preferred embodiment, the amino acid sequence of the mutant hemagglutinin differs from the amino acid sequence of wild type influenza A virus hemagglutinin in at least one of histidine-17 and aspartic acid-112, and further in at least one of threonine-115, glutamine-190, and leucine-226.

In yet another preferred embodiment, the mutant hemagglutinin is selected from the group consisting of HA[T155S], HA[E190D], HA[L226V], HA[E190D, L226V], HA[T155S,L226V], HA[T155S,L226V,H17Q], HA[T155S,L226V,D112G], and HA[T155S,E190D].

In another aspect, the vector of the invention further comprises a targeting molecule.

In a preferred embodiment, the targeting molecule is selected from the group consisting of a viral envelope protein, an antibody, an antibody domain, an antigen, a T-cell receptor, a cell surface receptor, a cell surface adhesion molecule, a major-histocompatibility locus protein, a chimeric protein comprising at least a portion of Myc protein, a chimeric protein comprising at least a portion of Tva protein, a chimeric protein comprising at least a portion of EGF, and a peptide selected by phage display that binds specifically to a defined cell.

In another aspect, the vector of the invention comprises at least one additional component.

In a preferred embodiment, the additional component is selected from the group consisting of a nucleic acid, an antisense nucleic acid, a gene, a protein, a peptide, a Vpr protein, an enzyme, an intracellular antagonist of HIV, a radionuclide, a cytotoxic compound, an antiviral agent, and an imaging agent.

In another aspect, the vector of the invention is selected from the group consisting of an enveloped virus and a liposome.

Also included in the invention is a method of producing a lipid-containing vector. The method comprises pseudotyping an enveloped virus with a mutant influenza A virus hemagglutinin, wherein the mutant hemagglutinin comprises at least one amino acid substitution at residues threonine-115, glutamine-190, and leucine-226 in the receptor binding pocket of the hemagglutinin, and further wherein the substitution substantially abrogates binding of the hemagglutinin to a sialic acid containing receptor, and co-pseudotyping the virus with a targeting molecule.

In one aspect, the vector comprises an additional component.

In another aspect, the amino acid substitution is selected from the group consisting of a change from threonine to serine at residue 155, a change from glutamine to asparagine at residue 190, and a change from leucine to valine at residue 226.

In another aspect, the vector comprises an amino acid substitution from threonine to serine at residue 155, and a second amino acid substitution from leucine to valine at residue 226.

In yet a further aspect, the targeting molecule is selected from the group consisting of a viral envelope protein, an antibody, an antibody domain, an antigen, a T-cell receptor, a cell surface receptor, a cell surface adhesion molecule, a major histocompatibility locus protein, a chimeric protein comprising at least a portion of Myc protein, a chimeric protein comprising at least a portion of Tva protein, a chimeric protein comprising at least a portion of EGF, and a peptide selected by phage display that binds specifically to a defined cell.

In a preferred embodiment, the targeting molecule is a chimeric protein comprising at least a portion of Myc, at least a portion of Tva, and at least a portion of EGF.

In another preferred embodiment, the additional component is selected from the group consisting of a nucleic acid, an antisense nucleic acid, a gene, a protein, a peptide, a Vpr protein, an enzyme, an intracellular antagonist of HIV, a radionuclide, a cytotoxic compound, an antiviral agent, and an imaging agent.

The invention also includes an isolated nucleic acid encoding an influenza A virus hemagglutinin, wherein the nucleic acid comprises a mutation in the receptor binding pocket of the hemagglutinin, wherein the mutation substantially abrogates binding of the hemagglutinin to a sialic acid containing receptor, and further wherein the mutation does not affect the fusogenic capability of the hemagglutinin.

In one aspect, the mutation effects a conservative amino acid substitution.

In a preferred embodiment, the conservative amino acid is selected from the group consisting of threonine-155, glutamine-190, and leucine-226.

Also included is an isolated influenza A virus hemagglutinin wherein the hemagglutinin comprises a mutation which substantially abrogates binding of the hemagglutinin to a sialic acid containing receptor and further wherein the mutation does not affect the fusogenic capability of the hemagglutinin.

In addition, the invention includes a pseudotyped murine leukemia virus (MLV) comprising a mutant influenza A hemagglutinin, wherein the mutant hemagglutinin comprises a first mutation comprising a change from threonine to serine at amino acid 155, and further wherein the mutant hemagglutinin comprises a second mutation comprising a change from leucine to valine at amino acid 226, wherein the pseudotyped MLV expresses the mutant hemagglutinin and wherein the mutant hemagglutinin is in the envelope of the pseudotyped MLV.

In one aspect, the hemagglutinin further comprises a third mutation comprising an amino acid substitution which causes the mutant hemagglutinin to undergo low-pH induced conformational changes to a fusogenic form.

In a preferred embodiment, the third mutation comprises an amino acid substitution selected from the group consisting of a substitution from histidine to glutamine at amino acid 17 and a substitution from asparagine to glycine at amino acid 112.

The invention also includes a composition comprising a co-pseudotyped enveloped virus expressing a mutant hemagglutinin and a targeting molecule wherein the co-pseudotyped virus binds to a target cell expressing a receptor for the targeting molecule and further wherein the mutant hemagglutinin causes the virus to fuse with the target cell.

In addition, the invention relates to a mammalian cell comprising pseudotyped murine leukemia virus (MLV) comprising a mutant influenza A hemagglutinin, wherein the mutant hemagglutinin comprises a first mutation comprising a change from threonine to serine at amino acid 155, and further wherein the mutant hemagglutinin comprises a second mutation comprising a change from leucine to valine at amino acid 226, wherein the pseudotyped MLV expresses the mutant hemagglutinin and wherein the mutant hemagglutinin is in the envelope of the pseudotyped MLV.

The invention further relates to a mammalian cell comprising co-pseudotyped enveloped virus expressing a mutant hemagglutinin and a targeting molecule wherein the co-pseudotyped virus binds to a target cell expressing a receptor for the targeting molecule and further wherein the mutant hemagglutinin causes the virus to fuse with the target cell.

Also included in the invention is a method of targeting delivery of a component to a desired cell. The method comprises inserting a mutant, hemagglutinin and a targeting molecule on the surface of a vector, wherein the targeting molecule mediates binding of the vector to a targeting molecule-specific receptor on the cell, and further wherein the mutant hemagglutinin mediates membrane fusion of the vector with the membrane of the cell, thereby delivering the component to the cell.

In one aspect, the component is selected from the group consisting of a nucleic acid, an antisense nucleic acid, a gene, a protein, a peptide, a Vpr protein, an enzyme, an intracellular antagonist of HIV, a radionuclide, a cytotoxic compound, an antiviral agent, and an imaging agent.

BRIEF DESCRIPTION OF THE DRAWINGS

FIG. 3A is an image of an SDS-PAGE gel depicting the increased release of pseudotyped MLV(HA) virions from 293T cells transiently transfected to produce the pseudotyped virus. Pseudotyped virus comprising wild type HA was released into the culture supernatant upon incubation of the transiently transfected cells in the presence of increasing amounts of neuraminidase.

FIG. 3B is an image of an SDS-PAGE gel illustrating the increased release of pseudotyped MLV(HA[T155S]) into the culture supernatant upon incubation of transfected 293T cells in the presence of increasing amounts of neuraminidase.

FIG. 3C is an image of an SDS-PAGE gel depicting the lack of effect on virus release of neuraminidase treatment in cells infected with pseudotyped MLV(HA[T155S,L226V]). Incubation of transfected 293T cells in the presence of increasing amounts of neuraminidase did not result in increased virus release into the culture supernatant demonstrating that, unlike MLV pseudotyped with wild type HA, MLV(HA[T155S,L226V]) was released efficiently from the cells and further demonstrating that this virus had completely lost its ability to bind sialic acid.

FIG. 5A is a quartet of images which depict HeLa-PV cells which were used the cell-cell membrane fusion assay described elsewhere herein. HeLa-PV monolayers were transiently transfected with wild type HA and demonstrated cell-cell fusion as illustrated by formation of syncytia upon trypsin activation of surface HA and a brief exposure to low pH.

FIG. 5B is a quartet of images which depict HeLa-PV cells which were used in the cell-cell membrane fusion assay described elsewhere herein. HeLa-PV monolayers were transiently transfected with HA[T155S,L226V] and the cells demonstrated cell-cell fusion as illustrated by formation of syncytia upon trypsin activation of surface HA and a brief exposure to low pH. There was no observable difference in syncytia formation between cells transfected with wild type HA and cells transfected with mutant HA[T155S,L226V].

FIG. 5C is a quartet of images which depict HeLa-PV cells which were used in cell-cell membrane fusion assay described herein in the absence of HA, i.e., "mock" infected cells. There was no syncytia formation in these cells compared with cells transfected with wild type HA or HA[T155S,L226V].

FIG. 9 is a graph depicting the virus titers in A431 cells of various pseudotyped and co-pseudotyped MLVs demonstrating the ability of MLV (HA[T155S, L226V, D112G] TvaEGF) to infect A431 cells.

DETAILED DESCRIPTION OF THE INVENTION

Figure 1:
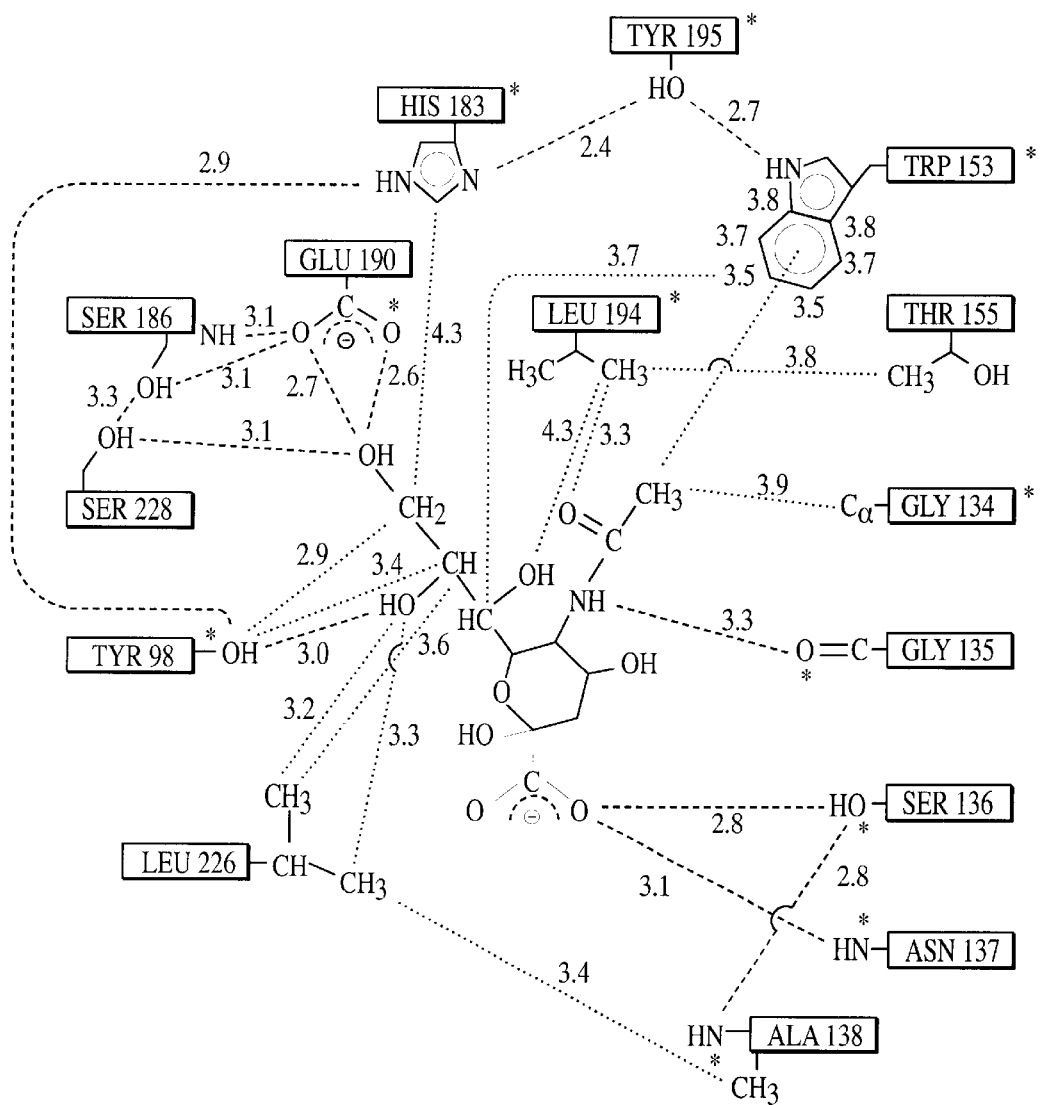
FIG. 1 is a schematic representation of the HA RBP, wherein the dotted lines indicate the hydrogen bonds formed by the side chains of the residues which comprise the RBP.

In the present invention pseudotyped murine leukemia virus (MLV) virions have been generated comprising mutant influenza virus A HA proteins. Each mutant HA had an altered amino acid in at least one of three highly-conserved residues of the receptor-binding pocket region of HA. Introduction of these mutations into HA resulted in a substantial loss of HA receptor-binding activity, that is, mutants of influenza A virus hemagglutinin (HA) were produced which lacked the ability to bind the cellular sialic acid containing receptor but which retained the fusogenic ability of wild type HA. Thus, the capacity of mutant HA, when pseudotyped into an enveloped virus, to induce fusion of the virion envelope with a cell membrane was preserved. Further, co-pseudotyping of MLV with the mutant HA and a chimeric ligand specific for the EGF receptor (Myc-Tva-EGF) enabled specific targeting of the co-pseudotyped MLV to a human epidermoid carcinoma cell over-expressing EGF receptor on its surface (A431 cells) and subsequent fusion of the co-pseudotyped virus envelope with the A431 cell membrane.

Thus, HA[T155S, L226V], which lacks the ability to bind to a cell membrane but retains HA fusogenic capacity, is useful as an agent which can be incorporated into the envelope of a virion and which is capable of inducing fusion of the virion envelope with the membrane of a target cell, wherein the fusion-inducing capacity of the agent is substantially independent of the tropism of the virion.

Furthermore, as indicated by the membrane fusion assay results disclosed herein, HA[T155S, L226V] can be used as an agent which can be incorporated into a cell membrane or into a liposome and which is capable of inducing fusion of the cell membrane or the liposome with the membrane of a target cell.

One skilled in the art will further appreciate that HA[T155S, L226V] may be used in combination with one or more targeting molecules, including, but not limited to, a viral envelope protein, an antibody, an antibody domain, an antigen, a T-cell receptor, a cell surface receptor, a cell surface adhesion molecule, a major histocompatibility locus protein, a peptide selected by phage display that binds specifically to a defined cell or tissue, a molecule which binds specifically to any of these molecules, or a molecule which binds specifically to any component exposed on the surface of a cell to produce a co-pseudotyped virus.

The HA of the invention is encompassed in a vector.

By the term "lipid containing vector" as used herein, is meant an enveloped virus or other lipid-containing vehicle, such as, but not limited to, a liposome, which vector facilitates transfer of a molecule or a compound into a cell. Examples of vectors include, but are not limited to, retroviruses, lentiviruses, spumaviruses, liposomes, and the like. A person skilled in the art will appreciate that the crucial feature of the vector as disclosed herein is the ability of the vector to present a targeting molecule and a fusogenic mutant HA which lacks appreciable HA-receptor binding activity, such that the lipid of the vector fuses with a target cell membrane thereby delivering a desired molecule or compound to a cell directed by the targeting molecule.

As noted herein, the mutant HA of the invention comprises a mutation in the receptor binding pocket of HA, such that the ability of the HA to bind a sialic acid containing receptor is substantially abrogated, while the fusogenic capacity of the HA is largely unaffected.

By the term "fusogenic capacity" as used herein to refer to HA, is meant the capacity of HA to cause two lipid layers to fuse together. By way of example only, such fusion may occur between the lipid layer of an enveloped virus vector and a cell membrane, or it may occur between the lipid layer of a liposome and a cell membrane.

By the term "sialic acid containing receptor" as used herein, is meant a cellular receptor molecule which comprises at least one sialic acid molecule.

By the term "substantially abrogated" as used herein to refer to binding of HA to a sialic acid containing receptor, is meant that the ability of HA to bind to a sialic acid containing receptor is essentially nullified, even though a minimal level of binding may be detectable.

By the term "receptor binding pocket of HA" as used herein, is meant that region of the HA1 subunit which comprises amino acids which are the contact points for binding of the HA to sialic acid.

By the term "pseudotyped virus," as the term is used herein, is meant an enveloped virus comprising at least one exogenous envelope molecule not typically present on the wild type virus envelope.

In a preferred embodiment, the pseudotyped virus is MLV comprising the HA molecule from influenza A virus and mutants thereof. For instance, in a preferred embodiment, pseudotyped MLV comprising wild type influenza A HA ie., MLV(HA), was able to agglutinate adult chicken erythrocytes.

By the term "co-pseudotyped virus" is meant an enveloped virus comprising at least two exogenous envelope molecules not normally present in the wild type virus. As it relates to the present invention, the co-pseudotyped virus contains both a targeting molecule which directs the host range and/or tissue tropism of the virus such that the virus adsorbs onto a desired target cell that it would otherwise not bind to, and also a fusogenic molecule which mediates membrane fusion and thereby causes the absorption of the virus into the target cell.

By the term "targeting molecule," as the term is used herein, is meant any of the above-listed molecules where such molecule binds to its ligand or receptor which is located on the surface of a target cell such as to bring the virus and cell membranes sufficiently close to each other that low-pH-induced conformational changes in the mutant HA mediates fusion of the two membranes.

In a preferred embodiment, the targeting molecule is Myc-Tva-EGF chimeric protein which targets the co-pseudotyped virus to cells expressing EGF receptor on their surface. However, the invention should not be construed to be limited to this particular target cell or to this particular targeting molecule or even to this targeting vehicle (i.e., MLV). Rather, the invention encompasses a wide variety of targeting molecules for which there are known specific receptor-ligand interactions and for cells which either normally express the ligand or receptor on their membranes or which can be made to express a targeting molecule receptor on their surface.

In preferred embodiments, the targeting molecule is selected from the group consisting of a viral envelope protein, an antibody, an antibody domain, an antigen, a T-cell receptor, a cell surface receptor, a cell surface adhesion molecule, a major histocompatibility locus protein, a chimeric protein comprising at least a portion of Myc protein, a chimeric protein comprising at least a portion of Tva protein, a chimeric protein comprising at least a portion of EGF, and a peptide selected by phage display that binds specifically to a defined cell.

Further, the invention is not limited solely to MLV as a target vehicle. Instead, the invention encompasses a wide variety of targeting gene delivery vehicles including, but not limited to, other retroviruses such as lentiviruses and spumaviruses, other enveloped viruses such as vesicular stomatitis virus, and non-viral lipid enveloped vectors such as liposomes, and the like.

One skilled in the art will appreciate that the vehicle of the invention can be used to delivery nucleic acids and other molecules and compounds of interest into the target cell. Numerous molecules and compounds can be delivered to cells using the vehicle of this invention. The invention therefore encompasses the delivery of nucleic acids which when expressed by the target cell, provide missing enzymes to the cells, are toxic to the cells thereby killing them or rendering them unable to grow or divide, or for example, provide a reporter molecule so that the cells may be identified or isolated.

The use of a vector having an envelope comprising HA[T155S, L226V] and a targeting molecule permits delivery of the vector to any cell which has on its surface a molecule to which the targeting molecule binds and fusion of the envelope of the vector with the membrane of the cell. Thus, the use of an enveloped vector comprising HA[T155S, L226V] and a targeting molecule permits specific delivery of vector, including, but not limited to, the contents of the envelope of the vector, to a target cell to which the targeting molecule can bind. By way of example, if the MLV(HA) virion comprising HA[T155S, L226V], as described herein, further comprises Eco-Env-EPO in the envelope thereof and a gene in the MLV genome thereof, then the gene can be delivered specifically to cells which express EPO receptor.

One skilled in the art will appreciate that the tropism of a vector comprising HA[T155S, L226V] can be altered by merely changing the targeting molecule; since this does not involve tampering with HA[T155S, L226V], there is essentially no risk of losing membrane fusion activity in the altered virion.

By "tropism," as that term is used herein, is meant the binding of a virus or a vector to a specific cell or tissue mediated by a specific ligand:receptor interaction.

In a preferred embodiment, as described herein, co-pseudotyped MLV comprising a mutant HA molecule and a chimeric targeting molecule (Myc-Tva-EGF) exhibited a tropism for A431 cells expressing EGF receptor on their membranes whereas the wild type MLV did not exhibit a tropism for these cells since it does not have molecule on its surface which enables the virus to bind to these cells.

Methods of Making Enveloped Virus Vectors

In essence, the method of making an enveloped virus vector comprises formation of a virus-like particle which comprises functional HA[T155S, L226V]. Hence, the method of making the enveloped virus vector of the invention requires expression of at least a competent portion of the genome of an enveloped virus in a cell which comprises functional HA[T155S, L226V]. The functional HA[T155S, L226V] may be a normal component of the cell or may be provided to the cell.

As used herein, the term "functional HA[T155S, L226V]" means a HA[T155S, L226V] molecule which is capable of facilitating fusion between the membrane or envelope with which the HA[T155S, L226V] molecule is associated and a membrane or envelope located in close proximity thereto under conditions of low pH. One skilled in the art will appreciate that a HA[T155S, L226V] molecule is functional if it is located in the outer membrane of a cell and oriented such that the portion of the HA[T155S, L226V] molecule which is capable of interacting with a membrane or envelope contacts the extracellular medium, or if it is located in the envelope of an enveloped virus or a virus vector having an envelope and oriented such that the portion of the HA[T155S, L226V] molecule which is capable of interacting with a membrane or envelope contacts the medium in which the virus or virus vector is suspended. A functional HA[T155S, L226V] molecule may be a full-length protein, such as that encoded by the genome of a normal cell, a fragment thereof, or a portion of a fusion protein comprising the HA[T155S, L226V] molecule.

As used herein, the term "competent portion of the genome of an enveloped virus" means the portion of the genome of the enveloped virus which, when expressed in a cell, results in formation of a virus-like particle.

The enveloped virus vector of the invention may be made using numerous variations of the method. Several non-limiting embodiments of such variations of the method are disclosed herein. The invention is not limited to the embodiments disclosed herein, but rather should be construed to encompass any and all variations which become evident as a result of the teaching provided herein.

Use of a Producer Cell Which Comprises HA[T155S, L226V]

In one embodiment of the method of making the enveloped virus vector of the invention, a producer cell which comprises HA[T155S, L226V] is provided at least a competent portion of the genome of an enveloped virus and is thereafter incubated under conditions which permit formation of the enveloped virus vector of the invention.

In a preferred embodiment, the producer cell line is 293T cells and the competent portion of the MLV virus is provided by a plasmid vector. The same or other vectors may also encode a reporter gene, β-galactosidase, pHIT60 and pHIT111.

In this embodiment of the method of making the enveloped virus vector of the invention, the identity of the producer cell which is used is not critical, except that the producer cell comprises HA[T155S, L226V] and the competent portion of the genome enables formation of virus-like particles when expressed in the producer cell. Examples of cells which comprise a particular virus receptor protein are found throughout the scientific literature. Examples of cells which enable the production of enveloped viral particles when the genome of an enveloped virus is expressed therein are also found throughout the scientific literature.

The manner of providing the competent portion of the genome of the enveloped virus is not critical except that, when the competent portion of the genome is expressed in a cell, the formation of enveloped virus-like particles must be enabled. The competent portion of the genome may be encoded by, for example, the genome of an enveloped virus, a plasmid, or a non-circularized nucleic acid. The competent portion of the genome may comprise, but is not limited to, a single-stranded RNA molecule, a double-stranded RNA molecule, a single-stranded DNA molecule, a double-stranded DNA molecule, or an RNA-DNA hybrid molecule. The enveloped virus may be any enveloped virus, and is preferably a retrovirus. MLV is preferred.

Conditions which enable formation of the enveloped virus vector of the invention are well known in the art for production of enveloped viral particles, including enveloped viruses, following infection of a cell with an enveloped virus. One of skill in the art would recognize that these conditions vary, depending upon the properties of the producer cell and the enveloped virus used in the method. Conditions which are useful for culturing particular enveloped viruses are well known in the art.

One of skill in the art would recognize that conditions which enable formation of the enveloped virus vector of the invention include conditions which enable expression of the competent portion of the genome of the enveloped virus, conditions which enable the presence of HA[T155S, L226V] in the membrane of the producer cell, and conditions which enable the formation of enveloped virus-like particles from the components of a producer cell which has been provided the competent portion of the genome. Further details regarding processes by which enveloped viral particles are formed following provision to a cell of a competent portion of the genome of an enveloped virus have been described in the art, for instance by Wiley (1985, In: *Fields' Virology*, pp. 45–52, Raven Press, New York).

In another embodiment of the method of making the enveloped virus vector of the invention, an additional component is provided to the producer cell, whereby, upon formation of the enveloped virus vector, the enveloped virus vector comprises the additional component. The additional component may be any molecule which can be provided to the cytoplasm or the membrane of the producer cell. By way of example, the additional component may be a nucleic acid, an antisense nucleic acid, a gene, a protein, a peptide, Vpr protein, as described (Connor et al., 1995, Virology 206:935–944; Naldini et al., 1996, Science 272:263–267), an enzyme, an intracellular antagonist of HIV, a radionuclide, a cytotoxic compound, an antiviral agent, and an imaging agent.

Inclusion of the additional component into the enveloped virus vector of the invention may be accomplished by directly coupling the additional component to the competent portion of the genome of the enveloped virus. For instance, if the competent portion of the genome is provided to the producer cell in the form of a plasmid, the plasmid may comprise a gene encoding an imaging agent, such as luciferase.

Inclusion of the additional component in the enveloped virus vector of the invention may also be accomplished by directly coupling the additional component to a nucleic acid encoding HA[T155S, L226V]. For instance, if HA[T155S, L226V] is provided to the producer cell in the form of a DNA molecule which encodes HA[T155S, L226V], an additional component comprising an additional protein may be provided to the producer cell by including the sequence of a gene encoding the additional protein in the DNA molecule which encodes HA[T155S, L226V], prior to provision thereof to the producer cell.

Use of a Producer Cell Which Does Not Normally Comprise HA[T155S, L226V]

In another embodiment of the method of making the enveloped virus vector of the invention, a producer cell is provided with at least a competent portion of the genome of an enveloped virus and a first virus receptor protein, and is thereafter incubated under conditions which permit formation of the enveloped virus vector of the invention. Unlike the method described hereinabove of making the enveloped virus vector of the invention, this embodiment does not employ a producer cell which normally comprises HA[T155S, L226V] prior to provision of such protein thereto.

In this embodiment of the method of making the enveloped virus vector of the invention, the manner of providing HA[T155S, L226V] is not critical. By way of example, HA[T155S, L226V] may be provided to the producer cell in the form of a protein embedded in the membrane portion of a membrane vesicle, in the form of a protein embedded in a liposome, in the form of a protein embedded in the membrane of a cell, in the form of a membrane-free solution of the protein, in the form of a solid protein, in the form of a protein embedded in the envelope of an enveloped virus, in the form of a protein embedded in the envelope of an enveloped virus vector of the invention, in the form of a nucleic acid encoding the protein, in the form of a DNA molecule encoding the protein, in the form of an RNA molecule encoding the protein, in the form of a virus having a nucleic acid which encodes the protein, in the form of an enveloped virus having a nucleic acid which encodes the protein, in the form of an enveloped virus vector of the invention having a nucleic acid which encodes the protein, and the like.

Preferably, HA[T155S, L226V] is provided to the producer cell in the form of a DNA molecule encoding the protein, more preferably in the form of a plasmid. These methods for delivering the virus receptor protein to the producer cell employ methods that have been well described in the scientific literature for providing a protein to a cell membrane. One skilled in the art of membrane protein biochemistry is able to adapt these known methods to provide HA[T155S, L226V] to a producer cell.

Other methods which were used but not described herein are well known and within the competence of one of ordinary skill in the art of molecular biology.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Cell-specific Targeting of Retroviral Vectors By a Two Component Glycoprotein System The experiments presented in this example may be summarized as follows.

Mutants of influenza A virus hemagglutinin (HA) were produced which lacked the ability to bind the cellular sialic acid receptor but which retained the fusogenic ability of wild type HA. These mutants were used to produce pseudotyped MLV (MLV(HA)) which lacked the ability to bind the HA receptor but which demonstrated the ability to fuse with the cell membrane. In addition, a chimeric epidermal growth factor (EGF) polypeptide (Myc-Tva-EGF) was used to co-pseudotype MLV such that the co-pseudotyped virus comprised both mutant HA and Myc-Tva-EGF in its envelope. The co-pseudotyped virus demonstrated the ability to fuse with cells which express the EGF receptor. Therefore, the present invention has separated, for the first time, the binding and fusing events necessary for transgene delivery onto two distinct molecules. Thus, the data disclosed herein demonstrate the production of a novel two component gene targeting system comprising a generic fusion mediator, i.e., an HA RBP mutant protein lacking sialic acid receptor binding while retaining fusogenic ability, and a targeting protein both of which are incorporated into a co-pseudotyped lentivirus.

The Materials and Methods used in the experiments presented in this example are now described.

Cell Lines

Human embryonic kidney 293T cells were maintained in high glucose Dulbecco's modified Eagle medium (DMEM, 4.5 g/L glucose) supplemented with 10% bovine calf serum; human epidermoid carcinoma A431 cells were maintained in high glucose DMEM supplemented with 10% fetal calf serum; human cervical carcinoma HeLa-PV cells were maintained in Iscove's MEM, supplemented with 10% fetal calf serum. All cell lines were also supplemented with 100 U/ml penicillin and 100 µg/ml streptomycin. A431 cells are described in Fabricant et al. (1977, Proc. Natl. Acad. Sci. USA 74:5584–5588), and HeLa-PV cells are known in the art.

Antibodies

A rabbit polyclonal antibody (R15B20) recognizing influenza A/Hong Kong/68 virus HA is described previously in Caton et al. (1991, J. Immunol. 147:1675–1686). Mouse ascites fluid containing the monoclonal antibody 9E10 which recognizes the Myc epitope was previously described by Evan et al., 1985, Mol. Cell. Biol. 5:3610–3616). Goat anti-MLV AKR capsid p30 antibody was purchased from Quality Biotech, Inc. (Camden, N.J.).

Plasmids and Expression

Plasmids pHIT60 (encoding MLV Gag-Pol) and pHIT111 (a packageable genome encoding the reporter gene β-galactosidase) are described in Soneoka et al. (1993, Nucl. Acid. Res. 23:628–633). Plasmids pHIT/G (encoding the VSV G protein), and pBS-HA, encoding the X-31 subtype of HA are known in the art. Plasmid pcDNA3 was purchased from Invitrogen (Carlsbad, Calif.).

Construction of HA Mutants

The HA gene was excised from pBS-HA by digestion with the restriction enzymes ClaI and KpnI, and the insert encoding HA was cloned into pcDNA3 to produce the plasmid pcDNA3-HA. PCR-based mutagenesis cassettes were cloned either directly into pcDNA3-HA, or into pBS-HA with subsequent cloning into pcDNA3 as described below herein. All mutagenesis was performed by two-step PCR (Ho et al., 1989, Gene 77:51–59) as previously described.

In order to generate the Thr-155 to Ser mutation (HA [T155S]), the first round PCR primers were 5'-TTGTCCAAATCAGG-3' (OS55; [SEQ ID NO:1]) with 5'-TATCTAGATCGACTAATACAC-3' (OS76; [SEQ ID NO:2]) and 5'-CCTGATTTGGACAA-3' (OS56; [SEQ ID NO:3]) with 5'-AATACGACTCACTATAG-3' (OS7; [SEQ ID NO:4]) using pBS-HA as the template. The resulting PCR fragments were mixed and amplified using OS76[SEQ ID NO:2] and OS7[SEQ ID NO:4] as primers. The fragment obtained from the second-round PCR was digested with BspDI and SalI and ligated with pBSKS+ (Stratagene, La Jolla, Calif.) vector DNA digested with BspDI and SalI.

For generation of the Glu-190 to Asp mutation in combination with Thr-155 to Ser (HA[T155S, E190D]), the Thr-155 to Ser mutation was made in a template of pcDNA3-HA[E190D]. First-round PCR primers were 5'-CCAGATTATGCCTCCCTTAGG-3' (OS295; [SEQ ID NO:5]) with 5'-CTTCCTGATTTGGACAACCAGTTC-3' (OS296; [SEQ ID NO:6]) for the 5' sense strand, and 5'-CTACTAGACAGACCCCTTACC-3' (OS297; [SEQ ID NO:7]) with 5'-GAACTGGTTGTCCAAATCAGGAAG-3' (OS298; [SEQ ID NO:8]) for the 3' antisense strand. The resulting PCR fragments were used as templates in the second-round PCR, using OS295[SEQ ID NO:5] and OS297 [SEQ ID NO:7] as primers. The fragment obtained from the second round PCR was digested with the restriction enzymes Bsu36I and PflmI, and cloned into pcDNA3-HA to generate pcDNA3-HA[T155S,E190D].

A cassette containing the Leu-226 to Val mutation was produced by first-round PCR from a pcDNA3-HA template. The primers for the 5' sense strand were 5'-GTTCAAGCATCAGGGAGAGTCACAGTC-3' (OS305; [SEQ ID NO:9]) and 5'-GCTTA TTCTACTAGACACACCCCTTACCCAG-3' (OS302; [SEQ ID NO:10]), and the primers for the 3' strand were 5'-CTGGGTAAGGGGTGTGTCTAGTAGAATAAGC-3' (OS301; [SEQ ID NO:11]) and 5'-TGGGA ATGCTTCCATTTGGAGTGATGC-3' (OS306; [SEQ ID NO:12]). The two products from the first-round PCR were used as templates in the second-round PCR reaction with OS305[SEQ ID NO:9] and OS306 [SEQ ID NO:12] as primers. The resulting PCR fragment was digested with the restriction enzymes PflmI and PpuIOI, and cloned into pBS-HA to produce pBS-HA[L226V]. A cassette containing the Leu to Val substitution was removed from pBS-HA [L226V] by digestion with PflmI and AgeI, and was subcloned into the following plasmids: pcDNA3-HA to make pcDNA3-HA[L226V]; pcDNA3-HA[T155S] to make pcDNA3-HA[T155S,L226V]; pcDNA3-HA[E190D] to make pcDNA3-HA[E190D,L226V].

Point mutations in HA[T155S,L226V] for raising the pH threshold of fusion were made according to the GeneEditor™ system ,(Promega Corp., Madison, Wis.). For the His to Gln mutation at residue 17 of HA1, the primers used were 5'-GCACCGCATGCTGTCCCAGGC-3' (OS470; [SEQ ID NO:13]) and 5'-GATAAATCTGGAGCCTCCAAGGGTGG TCTCGC GG-3' (OS442; [SEQ ID NO:14]). For the Asp to Gly substitution at residue 112 in HA2, the primers used were 5'-CATTTCCGAGCCAGTCAGGTC-3' (OS469; [SEQ ID NO:15]) and OS442 [SEQ ID NO:14]. For both mutations, pcDNA3HA[T155S, L226V] was used as a template. The mutagenesis was carried out as described by the supplier (Promega) and the mutations were confirmed by DNA sequence analysis.

Construction of Myc-Tva-EGF Chimeric Protein

The EGF minigene previously described by Stern et al. (1987, Science 255:321–324) was amplified from 72ΔAX, a plasmid which encodes an EGF-RSV-Env A chimera. The primers used for this amplification were 5'-CTTGGATCCAATTCAGAGGTTCAGAACTCTG-3' (OS393; [SEQ ID NO:16]) and 5'-TTTAT ACCGCGGGATCTGCAGGTCGAGTTCCC-3' (OS394; [SEQ ID NO:17]). These primers were designed such that a BamHI restriction site would be inserted at the 5' end, and a SacII restriction site would be inserted at the 3' end. These sites were utilized to swap the EGF minigene into Tva (Rong and Bates, 1995, J. Virol. 69:4847–4853) in place of the low density lipoprotein receptor (LDLR)-like motif, producing the construct pcDNA3-Myc-Tva-EGF. The EGF minigene portion of this construct was sequenced to ensure that no mutations had been introduced during the PCR amplification.

Analysis of Protein Expression From Constructs

All constructs described previously herein were tested for expression by transient transfection in 293T cells, using a standard $CaPO_4$ precipitation method (Wool-Lewis and Bates, 1998, J. Virol., 72:3155–3160). Forty-eight hours post-transfection, the transiently transfected 293T cells were lysed in Triton lysis buffer (50 mM Tris pH 8, 5 mM EDTA, 150 mM NaCl, 1% Triton X-100), and the lysates were subjected to SDS-PAGE (10% or 12.5%) under reducing conditions. After transferring the proteins onto nitrocellulose membranes, expression of proteins was assessed by Western blot analysis as previously described (Rong and Bates, 1995, J. Virol. 69:4847–4853).

Expression of HA was detected using a 1:2,000 dilution of R15B20 primary antibody, followed by a 1:20,000 dilution of a horseradish-peroxidase (HRP) conjugated goat anti-rabbit secondary antibody (Pierce, Rockford Ill.).

Expression of the Myc-Tva-EGF chimeric protein was detected using a 1:1,500 dilution of an anti-Myc primary antibody (9E10), followed by a 1:10,000 dilution of a HRP-conjugated goat anti-mouse secondary antibody (Pierce, Rockford, Ill.).

MLV gag-pol expression was detected using a 1/2,500 dilution of the anti-capsid goat polyclonal AKR P30

(Quality Biotech, Camden, N.J.), and a 1/20,000 dilution of HRP-conjugated rabbit anti-goat secondary antibody Pierce, Rockford, Ill.). All dilutions of antibodies were made in Blotto (phosphate buffered saline, PBS, containing 0.1% Tween-20 and 5% fat-free powdered milk).

Production of MLV(HA) Pseudotype

MLV pseudotypes were produced using a modified version of a transient packaging system (Soneoka et al., 1995, Nucleic Acids Res. 23:628–633). Briefly, 293T cells were seeded in 100 mm tissue culture plates at a density of $4 \times 10^6$ cells per plate one day prior to transfection. The cells were transiently transfected using a standard $CaPO_4$ precipitation method as described by Wool-Lewis and Bates (1998, J. Virol. 72:3155–3160) with 20 μg pcDNA3-HA, 10 μg pHIT111 and 10 μg pHIT60. Approximately 16 hours post-transfection, protein expression was induced by changing the cell medium to fresh growth medium containing 10 mM sodium butyrate. Approximately 10–12 hours after sodium butyrate addition, Clostridium perfringens neuraminidase (Sigma Chemical Co., St. Louis, Mo.) was added from a 2.5 U/ml stock to a final concentration of between 1 and 25 mU/ml. Forty-eight hours post-transfection, a second aliquot of neuraminidase (NA) was added to yield a final amount of NA in the mixture to between 2 and 50 mU/ml. One hour, later virus-containing culture supernatants were clarified by low speed centrifugation (10 minutes at 1,500 ×g) and the supernatants were filtered through a 0.45 μm filter. The resultant virus was concentrated by ultracentrifugation either through a 20% sucrose cushion at 237,000 ×g (for biochemical analysis) or without sucrose at 50,000 ×g for 90 minutes (for infection). Pelleted virus was either resuspended overnight at 4° C. in a small volume of approximately 100–200 μl in NTE (100 mM NaCl, 50 mM Tris, 1 mM EDTA, pH 7.2) for infection or in PBS for binding assays, or the virus were lysed in 100 μl RIPA buffer (140 mM NaCl, 10 mM Tris pH 8, 5 mM EDTA, 1% sodium deoxycholate, 1% Triton X-100, 0.1% SDS) for Western blot analysis.

Receptor Binding Assay

Concentrated viral stocks were placed in two-fold dilution series (in PBS) in 96-well microtiter plates (50 μl per well). Washed chicken erythrocytes (0.5% in PBS) were added to each well (50 μl per well), and after gentle mixing, hemagglutination was left to proceed at room temperature for 1 hour. The amount of virus bound was measured in terms of the number of hemagglutinating units (HAU) per ml. These numbers were recorded as the reciprocal value of the dilution factor of the last well in which hemagglutination was observed. PBS was used as a negative control, and roughly equivalent amounts of HA were used in the assay, based on Western blot analysis of virions.

293 T-cell Infections

Concentrated viral stocks to be used for infection were first activated by incubating the virus for 10 minutes at 37° C. in the presence of 10 μg/ml TPCK-trypsin (Sigma Chemical Co., St. Louis, Mo.), followed by the addition of 50 μg/ml soybean trypsin inhibitor (STI; Sigma Chemical Co., St. Louis, Mo.). These trypsinized viral stocks were aliquoted and stored at −80° C. until use. The viral stock aliquots were freeze-thawed only once, and then discarded.

293T cells were seeded in 6-well dishes at a density of $3 \times 10^5$ cells/well one day prior to infection. Infections were carried out in 1 ml of maintenance medium containing concentrated, trypsin-activated virus. Infections were left to proceed overnight, and the cells were re-fed with an additional 1 ml of fresh medium on the following day, and then the cells were left to grow to confluence. Confluent cell monolayers were washed in PBS, fixed in 2% paraformaldehyde (10 minutes at room temperature), and then stained for β-galactosidase activity with X-Gal solution (35 mM $K_3FE(CN)_6$, 35 mM $K_4FE(CN)_6 \cdot 3H_2O$, 2 mM $MgCl_2$, and 0.1% 5-bromo-4-chloro-3-indolyl-β-D-galactopyranoside [X-Gal] in PBS) as described by Soneoka et al. (1995, Nucleic Acids Res. 23:628–633). Infectious titers were determined by microscopic enumeration of β-galactosidase expressing (blue) cells, and expressed as the number of infectious units per milliliter of concentrated virus stock (IU/ml).

Acid By-pass Infection of A431 Cells

A431 cells were seeded in 6-well dishes at a density of $1.5 \times 10^5$ cells/well the day before infection. The following day, cells were washed with serum-free DMEM, and starved of serum in this medium for 4 to 5 hours. Serum-starved cells were cooled on ice for 20 to 30 minutes, and the medium was aspirated and replaced with 1 ml of ice-cold virus binding medium (RPMI, 0.2% bovine serum albumin (BSA), 10 mM HEPES, pH 7) containing an aliquot of concentrated virus stock. Virus was left to bind to the cells on ice for 1 hour, then the virus-containing binding buffer was removed and replaced with 1 ml of fusion medium (identical to virus binding medium, but at pH 4.8) which was pre-warmed to 37° C. After 15 minutes incubation at 37° C., the fusion medium was removed, and the cells were washed in DMEM supplemented with 10% FCS. Infected cells were left to grow to confluence in this medium, and then the cells were fixed and stained for β-galactosidase activity as described above.

EGF Binding Inhibition Studies

Experiments in which EGF was used to block infection were carried out as described previously herein for the acid by-pass experiments, but with a 50 minute incubation of serum-starved cells at 4° C. wherein binding medium containing various concentrations of EGF was carried out prior to the addition of virus (without removing the EGF).

Spin-Infections

Cells were seeded in 6-well dishes the day before infection as described above, and after serum starvation for 4 to 5 hours, the media was removed and replaced with 1.5 ml serum-free DMEM containing 10 mM HEPES. Aliquots of concentrated virus (5 to 30 μl) were added to each well, and the plates were centrifuged at 1,300×g for 2 hours at room temperature. DMEM supplemented with 10% fetal calf serum was added to each well (1 ml), and after incubation for 1–2 hours at 37° C. in the presence of 5% $CO_2$, the media was replaced with 2 ml DMEM supplemented with 10% fetal calf serum. Cells were allowed to grow to confluence, at which point they were fixed and stained for β-Gal activity as described above.

Experiments in which EGF was used to block infection were carried out as described for the spin-infection, but with a 60-minute incubation of serum-starved cells at 37° C. in 1.5 ml serum-free DMEM containing 10 mM HEPES containing various concentrations of EGF prior to the addition of virus.

Experiments wherein the effects of adding anti-EGF monoclonal antibody (α-EGF-10, Sigma Chemical Co., St. Louis, Mo.) on virus infection were determined were carried out as described previously herein for the spin infections, except that the virus was mixed gently for 1 hour at room temperature in 0.5 ml serum-free DMEM, 10 mM HEPES, containing α-EGF-10 at concentrations ranging from 0 to 10 μg/ml. The volume was than increased to 1.5 ml with serum-free DMEM, 10 mM HEPES, and this medium was used for spin-infections as described above.

The Results of the experiments presented in this example are now described.

HA Receptor Binding Pocket Mutants Are Expressed at Wildtype Levels In 293T Cells The available crystal structure of X-31 HA complexed with its receptor, sialic acid (Weis et al., 1988, Nature 333:426–431), facilitated the design of point mutations that would potentially reduce or ablate receptor binding. FIG. 1 illustrates a schematic representation of the HA RBP, with dotted lines indicating the hydrogen bonds formed by the side chains of the residues which comprise the RBP. Based on their hydrogen bonding interactions with sialic acid, three residues were chosen for mutation: Thr-155, Glu-190 and Leu-226. These residues were substituted such that the part of the side chain which was involved in hydrogen bonding was shortened. Thus, Thr-155 was mutated to Ser, Glu-190 to Asp, and Leu-226 to Val. The rationale behind this approach was that the shortened side chains should increase the hydrogen bond lengths and weaken the hydrogen bonds formed compared with the wild type HA RBP thereby leading to a potentially reduced or ablated sialic-acid binding capability. In addition, since these mutations comprise conservative amino acid substitutions, they were expected to be less likely to severely perturb the HA structure and its fusogenic function.

Figure 2:
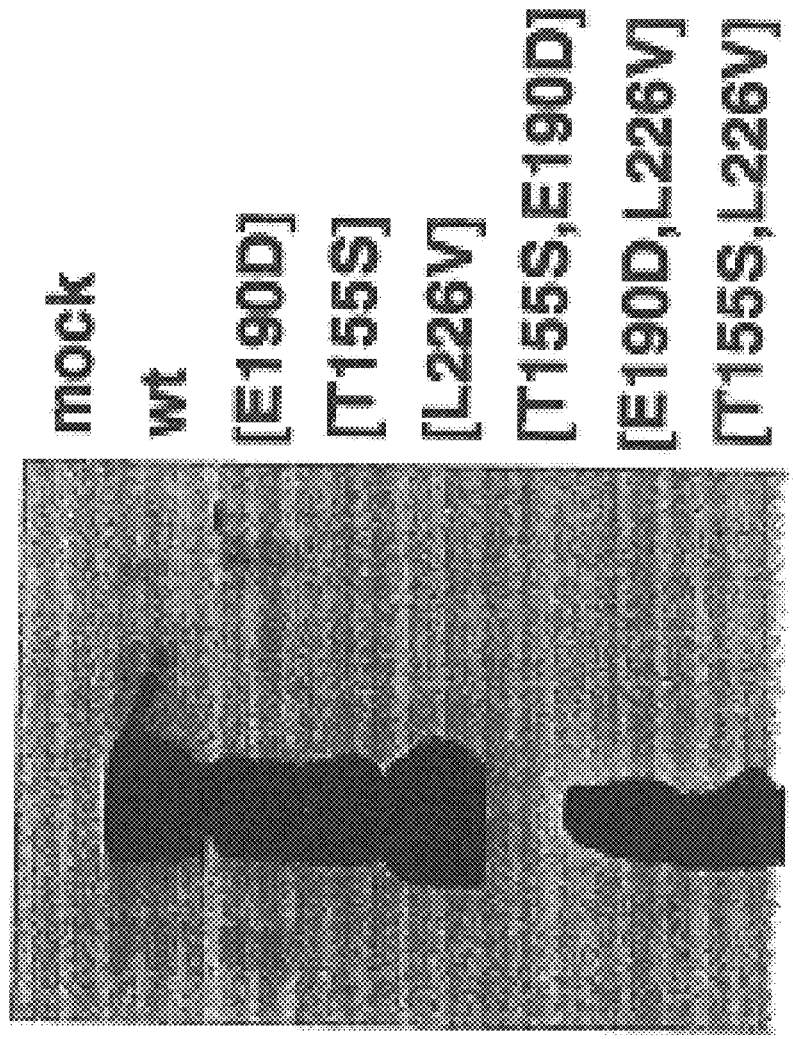
FIG. 2 is an image of an SDS-PAGE gel depicting the expression of constructs encoding HA, both wild type HA and mutants thereof, in transiently transfected 293T cells.

Single point mutants and double mutants in HA were made for all three residues using PCR-based mutagenesis, and the constructs encoding the mutants were analyzed for expression of HA by transient transfection in 293T cells. All of the mutant HA's were expressed at levels comparable to wild type HA, with the exception of the double mutant HA[T155S,E190D] (FIG. 2). The low expression level observed for the HA[T 155S,E190D] mutant was probably due to misfolding and intracellular degradation of this protein.

HA RBP Mutants Pseudotyped Efficiently Into MLV and Some Were Binding Mutants

Once the cellular expression of the HA mutants was demonstrated, a transient transfection system in 293T cells was used to produce MLV(HA) pseudotypes. This pseudotyping system has been described previously (Wool-Lewis and Bates, 1998, J. Virol. 72:3155–3160) and was adapted in this instance by the use of the influenza HA expression vector and the addition of a bacterial neuraminidase treatment of producer cells prior to harvesting virus from the culture supernatants. The reasoning behind the addition of neuraminidase being that, in addition to HA, influenza A virions have a second, less abundant glycoprotein in the viral membrane, the neuraminidase (NA). Mutant influenza A virions which lack NA are unimpaired in all stages of the infectious cycle, up to the budding of virions. However, NA-deficient budded virions remain attached to the host cell surface unless an exogenous bacterial neuraminidase is added (Liu et al., 1995, J. Virol. 69:1099–1106). Since the pseudotyped MLV(HA) virions lack NA, it was predicted that release of budded pseudotyped virions from producer cells would require the presence of exogenous (in this case, bacterial) neuraminidase. This need for exogenous NA was confirmed for wild type MLV(HA): no virions could be detected in culture supernatants in the absence of neuraminidase, but increasing amounts of virus were detected with increasing neuraminidase concentrations (FIG. 3A). These differences in virion yields were not due to differential expression of HA in the producer cells, since the total cellular expression levels of HA were comparable at all concentrations of neuraminidase used.

Almost all of the HA mutants tested in this pseudotyping system behaved like wild type HA, with the exception of HA[T155S] and HA[T155S,L226V]. Moderate amounts of MLV(HA[T155S]) virions were harvested in the absence of neuraminidase, but increasing virus yield was nevertheless observed in a neuraminidase-dependent manner (FIG. 3B). This suggested that, while HA[T155S] was still able to bind sialic acid, this binding capability was impaired relative to wild type HA. For the HA[T155S,L226V] mutant, this virus was produced in a neuraminidase-independent manner (FIG. 3C), which suggested that this mutant had completely lost its ability to bind sialic acid. The apparent shift in molecular weight of HA visible on some of these Western blots with increasing neuraminidase concentrations is due to loss of sialic acid residues from the complex N-linked glycans present on the HA.

Figure 4A:
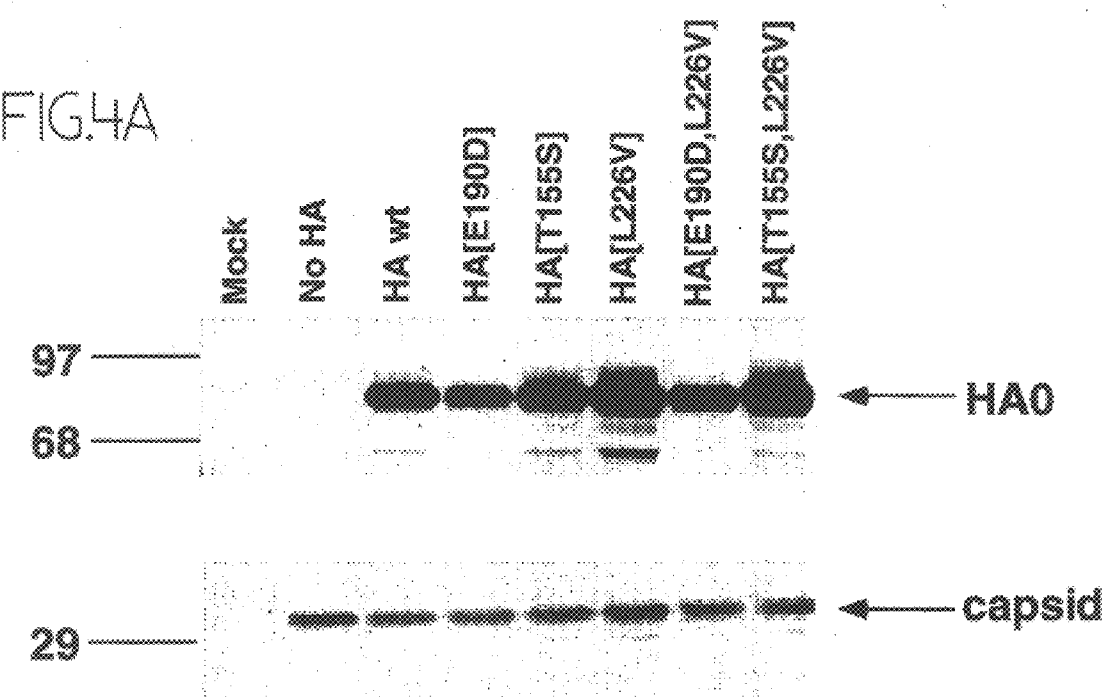
FIG. 4A is an image of a Western blot of purified MLV pseudotyped virions having various HA proteins incorporated therein. The sample of lane 1 was obtained from cells that did not produce any virions. The virion sample of lane 2 did not contain any HA. The virion sample of lane 3 comprised wild type HA. The virion of lanes 3 through 7 comprised various altered HA proteins.
Figure 4B:
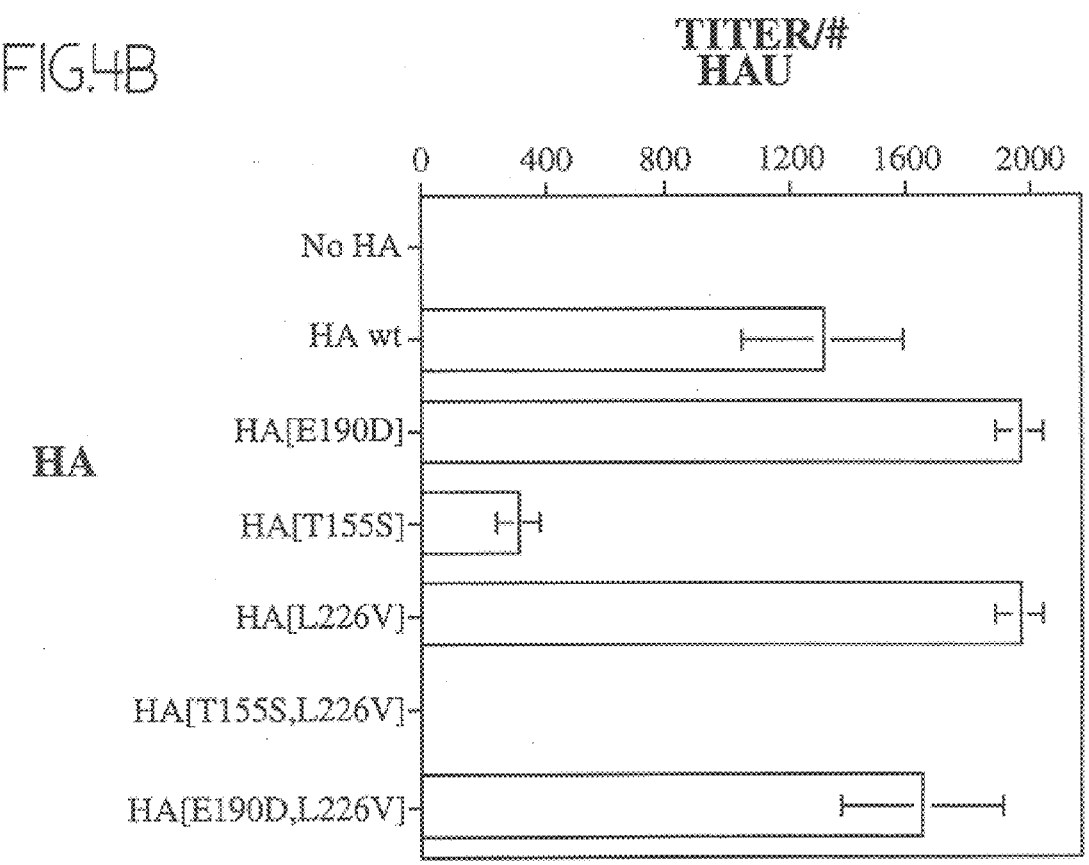
FIG. 4B is a graph which depicts the capacity of virions comprising no HA, wild type HA, or an altered HA protein to bind to adult chicken erythrocytes. "Mock" refers to virions which were subjected to the virion production procedures described herein, except that no nucleic acid encoding the virion proteins or an HA protein was used.

To confirm that the apparent reductions in sialic-acid binding for HA[T155S] and HA[T155S,L226V] in the pseudotyping assay were not artifactual, and not due to a change in receptor specificity (e.g., 2–3 linked versus 2–6 linked sialic acid) additional binding studies were performed. Reduced binding due to factors other than lack of sialic acid-binding was of particular concern with regard to HA[T155S,L226V] in light of previous observations that the residue at position 226 can in some instances determine receptor linkage specificity for HA (see, e.g., Rogers et al., 1983, Nature 304:76–79). Therefore, a hemagglutination assay was performed to assess the abilities of the MLV(HA) pseudotypes to agglutinate adult chicken erythrocytes, which are known to carry both 2–3 and 2–6 linked sialic acid moieties. Roughly equivalent amounts of HA were used in this assay, based on Western blot analysis of concentrated virions (FIG. 4A). The binding abilities of the MLV(HA) pseudotypes reflected those suggested by the pseudotyping assay: MLV(HA[T155S,L226V]) exhibited no sialic acid binding; MLV(HA[T155S]) exhibited reduced binding, and all other MLV(HA) pseudotypes displayed wt-like binding (FIG. 4B).

The HA[T155S,L226V] Mutant Can Mediate Membrane Fusion

A cell-cell fusion assay was performed to assess the ability of the mutant HA's to mediate membrane fusion. This assay was used since the nature of the membrane in which the HA is anchored (viral versus cellular) does not affect its ability to mediate membrane fusion in a low-pH environment, provided the target membranes are in close enough proximity.

Figures 6A, 6B, 6C:
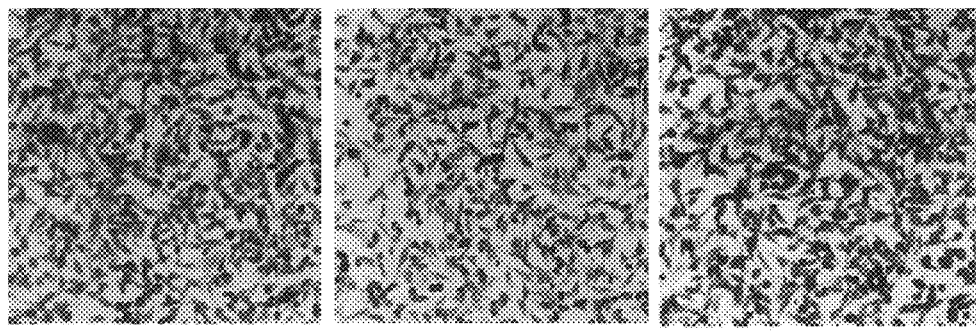
FIG. 6 is an image(comprising nine panels) depicting the results of cell-cell fusion experiments performed as described elsewhere herein illustrating the effect of varying pH (4.8, 5.34, and 5.58) on fusion of HeLa-PV cells transiently transfected with the following constructs: mock (no HA), HA wt, and HA[T155S,L226V]. Cells transfected with HA[T155S,L226V] demonstrated fusion characteristics identical to cells transfected with wild type HA in that there was no syncytia formation above pH 5.3.
Figures 6D, 6E, 6F:
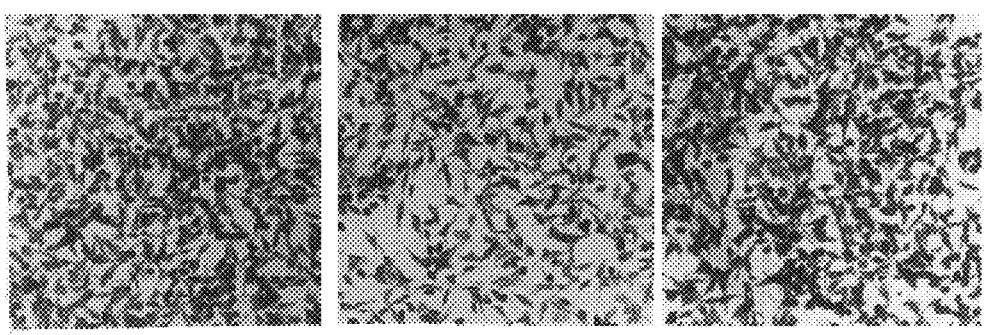
Figures 6G, 6H, 6I:
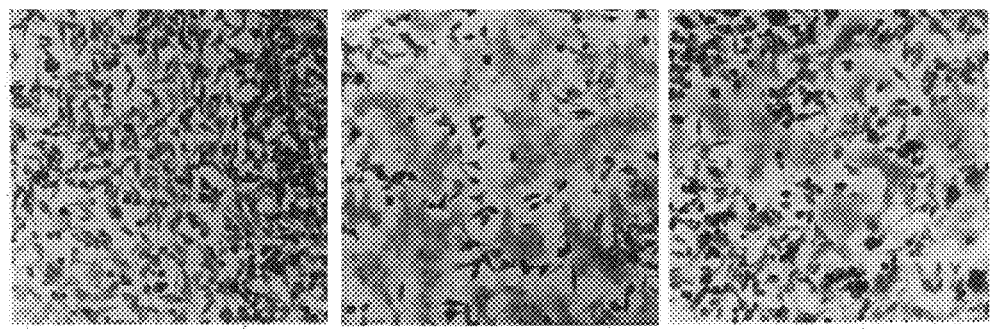

The HA mutant that was defective for receptor binding, HA[T155S,L226V], was tested for its ability to mediate membrane fusion in a cell-cell fusion assay. HeLa-PV cell monolayers transiently transfected with either wt HA or HA[T155S,L226V] both formed clearly visible syncytia following trypsin activation of the surface HA, and brief exposure to low pH (FIGS. 5A and 5B). There was no difference in either the number or size of syncytia observed using the mutant compared with wild type HA. In addition, the pH threshold of the HA[T155S,L226V]-mediated membrane fusion was similar to wt HA, with no fusion occurring above pH 5.3 (FIG. 6). Together, these results suggest that while the receptor binding activity of HA[T155S,L226V] was abolished, the fusion activity of this mutant was conserved.

It was next determined whether the mutant HA[T155S, L226V] would function to mediate fusion in the context of an MLV virion. The initial pseudotyping experiments had demonstrated that 293T cells would carry some glycoconjugate(s) on their surfaces that would bind MLV (HA), and it was hypothesized that whatever this/these glycoconjugate(s) were, at least one would serve as a functional receptor that would facilitate endocytosis of incoming virus.

Figure 7A:
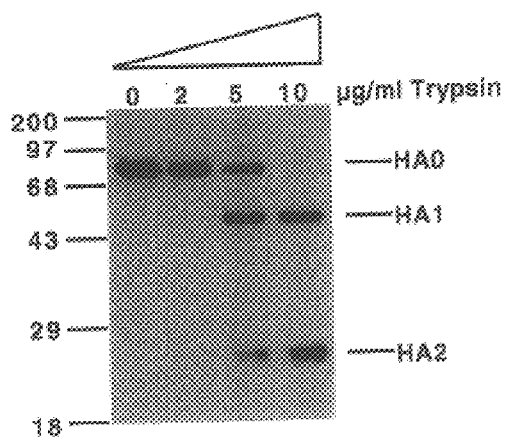
FIG. 7A is an image of a protein gel depicting the effect of increasing trypsin concentrations on cleavage of HA0 precursor into HA1 and HA2 subunits.
Figure 7B:
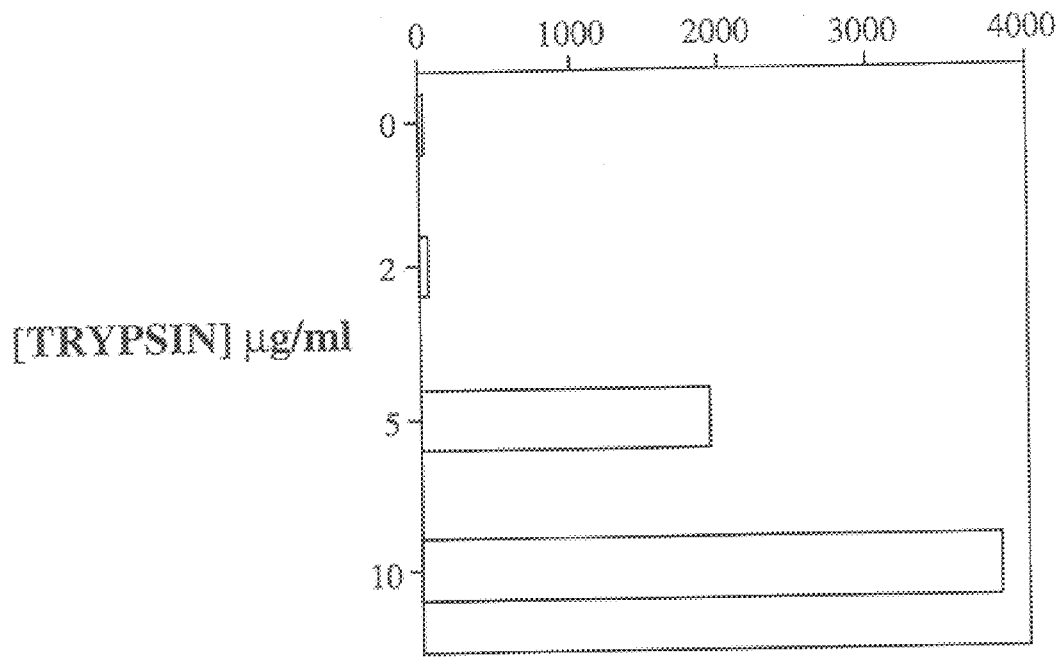
FIG. 7B is a graph illustrating the fact that the ability of MLV(HA) virus to infect 293T cells is dependent upon trypsin activation of HA.

Concentrated stocks of MLV(HA) and MLV(HA[T155S, L226V]) pseudotyped virions were used to infect 293T cells. Pseudotype MLV(HA) was able to infect 293T cells efficiently, and this infectivity was dependent on the extent of trypsin activation of the virus (FIG. 7). In contrast, MLV(HA[T155S,L226V]) was unable to infect 293T cells, apparently due to the lack of receptor binding activity by the mutant protein.

HA[T 155S,L226V] Can Facilitate Targeted Infection In an MLV Pseudotype

Mutant HA[T 155S,L226V] was co-pseudotyped into MLV with a chimeric epitope-tagged, membrane-bound form of the ligand for epidermal growth factor receptor (EGF), Myc-Tva-EGF. This targeting molecule was made by replacing the LDL-receptor like region of Tva with the EGF minigene, leaving the cytoplasmic tail, transmembrane region, and a proline-rich "hinge" region of Tva. Tva was utilized as a platform to present ligand for two reasons: firstly, Tva is able to pseudotype efficiently into MLV virions, and, secondly, it was reasoned that the proline-rich hinge of Tva would facilitate good presentation of EGF, since this region is known to be rich in O-linked carbohydrates, a feature which tends to make proteins more rigid.

Figure 8A:
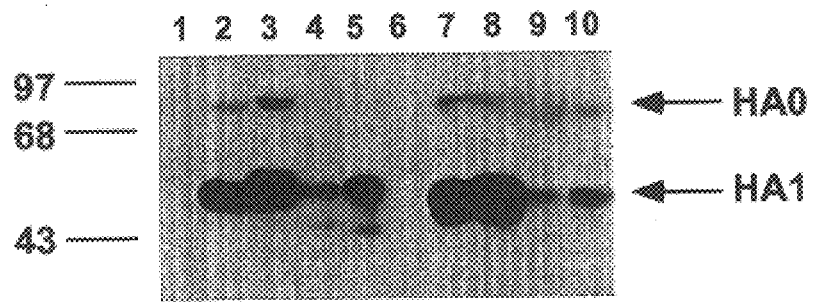
FIG. 8A is an image of a Western blot using R15B20 (anti-HA) to detect the presence of HA in various pseudotyped MLVs.
Figure 8B:
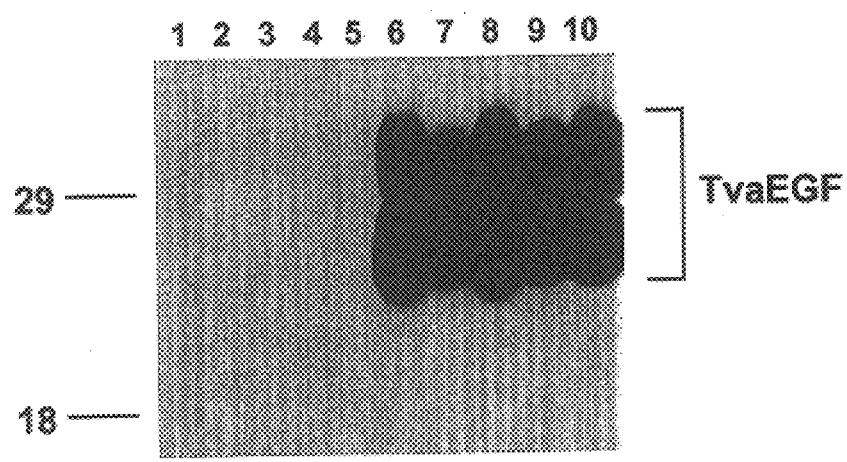
FIG. 8B is an image of a Western blot using anti-Myc antibody (9E10) to demonstrate the presence or absence of the Myc-Tva-EGF chimeric protein in various pseudotyped MLVs.
Figure 8C:
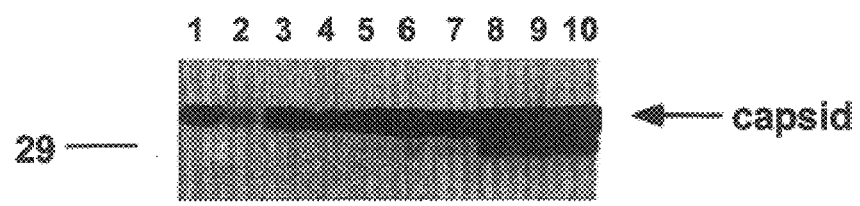
FIG. 8C is an image of a Western blot using anti-MLV capsid antibody (AKR p30) to demonstrate the presence or absence of the MLV capsid p30 protein in various pseudotyped MLVs.

Concentrated co-pseudotyped virus stocks were activated by brief trypsin treatment which was milder than that used in prior experiments, since at higher trypsin concentrations, it appeared the Myc-Tva-EGF chimera was being clipped off the virions. Western blot analysis of these virions demonstrated that HA and Myc-Tva-EGF were able to co-pseudotype into MLV (FIGS. 8A and 8B). These co-pseudotyped virions were used to infect A431 cells (a human epidermoid carcinoma cell line which over-expresses EGF receptor) after starving cells of serum in order to up-regulate surface levels of EGF receptor (serum EGF binding triggers internalization of EGF receptor). These infections were relatively inefficient unless they were carried out in the context of an acid bypass, so that virus-cell membrane fusion occurred at the cell surface. Apparently, the need for the acid bypass was that the intracellular compartment into which EGF-receptor bound virions were being endocytosed in the A431 cells was not at a low enough pH for efficient fusion activity of the HA.

Additional Mutations Lower the pH Threshold of HA and Allow EGF Directed Infection To address whether the requirement for an acid by pass step was indeed due to the EGF receptor not cycling to an endosomal compartment with a sufficiently low pH to trigger the requisite HA conformational changes, point mutations were introduced into HA[T155S,L226V] that are known to raise the pH threshold of fusion in the HA subtype which was being used for the experiments disclosed herein.

The mutations, a His to Gln substitution in residue 17 of HA1 or an Asp to Gly mutation at residue 112 of HA2, raise the fusion pH threshold by approximately 0.6 and 0.3 pH units, respectively, in wild type X-31 HA (Steinhauer et al., 1996, Proc. Natl. Acad. Sci. USA 93:12873–12878).

Figure 10:
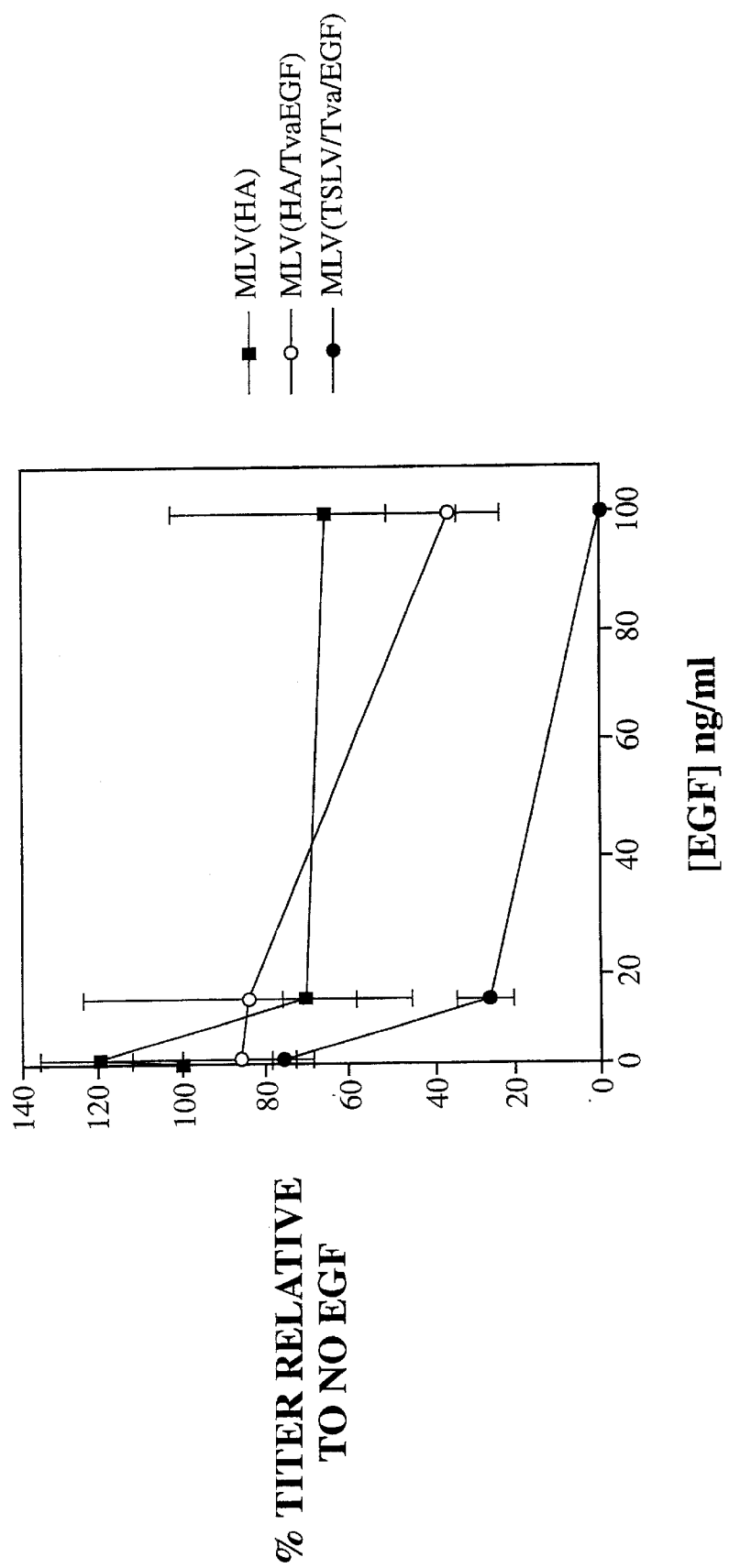
FIG. 10 is a graph illustrating the ability of soluble EGF to specifically inhibit the infection of A431 cells by various co-pseudotyped MLVs.

These additional mutations enabled efficient infection of A431 cells without the use of an acid bypass (FIG. 9). Thus, the co-pseudotyping experiments disclosed herein demonstrate that the mutant HA's lack the ability to bind which could be supplied by the Myc-TvaEGF targeting molecule and that the mutant HA retained fusogenic activity thus enabling infectivity as was expected in this two component target/fusion system. This infection was specifically mediated through interaction of Myc-Tva-EGF with EGF receptor, since infection was inhibited in a dose-dependent manner by soluble EGF (FIG. 10).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A lipid-containing vector which fuses to a cell membrane, said vector comprising a mutant hemagglutinin, wherein said hemagglutinin comprises a mutation in the receptor binding pocket of said hemagglutinin, wherein said mutation substantially abrogates binding of said hemagglutinin to a sialic acid containing receptor, and further wherein said mutation does not affect the fusogenic capacity of said hemagglutinin.

2. The vector of claim 1, wherein said hemagglutinin is an influenza A virus hemagglutinin.

3. The vector of claim 2, wherein said mutant hemagglutinin comprises a mutation in at least one amino acid in the receptor-binding pocket of said influenza A virus hemagglutinin.

4. The vector of claim 2, wherein the amino acid sequence of said mutant hemagglutinin differs from the amino acid sequence of wild type influenza A virus hemagglutinin in at least one of histidine-17, aspartic acid-112, threonine-115, glutamine-190, and leucine-226.

5. The vector of claim 4, wherein the amino acid sequence of said mutant hemagglutinin differs from the amino acid sequence of wild type influenza A virus hemagglutinin in at least one of histidine-17 and aspartic acid-112, and further in at at least one of threonine-115, glutamine-190, and leucine-226.

6. The vector of claim 3, wherein said mutant hemagglutinin is selected from the group consisting of HA(T155S), HA(E190D), HA(L226V), HA(E190D, L226V), HA(T155S,L226V), HA(T155S,L226V,H17Q), HA(T155S, L226V,D112G), and HA(T155S,E190D).

7. The vector of claim 1, further comprising a targeting molecule.

8. The vector of claim 7, wherein said targeting molecule is selected from the group consisting of a viral envelope protein, an antibody, an antibody domain, an antigen, a T-cell receptor, a cell surface receptor, a cell surface adhesion molecule, a major histocompatibility locus protein, a chimeric protein comprising at least a portion of Myc protein, a chimeric protein comprising at least a portion of Tva protein, a chimeric protein comprising at least a portion of EGF, and a peptide selected by phage display that binds specifically to a defined cell.

9. The vector of claim 1, wherein said vector comprises at least one additional component.

10. The vector of claim 9, wherein said additional component is selected from the group consisting of a nucleic acid, an antisense nucleic acid, a gene, a protein, a peptide, a Vpr protein, an enzyme, an intracellular antagonist of HIV, a radionuclide, a cytotoxic compound, an antiviral agent, and an imaging agent.

11. The vector of claim 1, wherein said vector is selected from the group consisting of an enveloped virus and a liposome.

12. A method of producing a lipid-containing vector, said method comprising pseudotyping an enveloped virus with a mutant influenza A virus hemagglutinin, wherein said mutant hemagglutinin comprises at least one amino acid substitution at residues threonine-115, glutamine-190, and leucine-226 in the receptor binding pocket of said hemagglutinin, and further wherein said substitution substantially abrogates binding of said hemagglutinin to a sialic acid containing receptor, and co-pseudotyping said virus with a targeting molecule.

13. The method of claim 12, wherein said vector comprises an additional component.

14. The method of claim 12, wherein said amino acid substitution is selected from the group consisting of a change from threonine to serine at residue 155, a change from glutamine to asparagine at residue 190, and a change from leucine to valine at residue 226.

15. The method of claim 12, wherein said vector comprises an amino acid substitution from threonine to serine at residue 155, and a second amino acid substitution from leucine to valine at residue 226.

16. The method of claim 12, wherein said targeting molecule is selected from the group consisting of a viral envelope protein, an antibody, an antibody-domain, an antigen, a T-cell receptor, a cell surface receptor, a cell surface adhesion molecule, a major histocompatibility locus protein, a chimeric protein comprising at least a portion of Myc protein, a chimeric protein comprising at least a portion of Tva protein, a chimeric protein comprising at least a portion of EGF, and a peptide selected by phage display that binds specifically to a defined cell.

17. The method of claim 16, wherein said targeting molecule is a chimeric protein comprising at least a portion of Myc, at least a portion of Tva, and at least a portion of EGF.

18. The method of claim 13, wherein said additional component is selected from the group consisting of a nucleic acid, an antisense nucleic acid, a gene, a protein, a peptide, a Vpr protein, an enzyme, an intracellular antagonist of HIV, a radionuclide, a cytotoxic compound, an antiviral agent, and an imaging agent.

19. An isolated nucleic acid encoding an influenza A virus hemagglutinin, wherein said nucleic acid comprises a mutation in the receptor binding pocket of said hemagglutinin, wherein said mutation substantially abrogates binding of said hemagglutinin to a sialic acid containing receptor, and further wherein said mutation does not affect the fusogenic capacity of said hemagglutinin.

20. The isolated nucleic acid of claim 19, wherein said mutation effects a conservative amino acid substitution.

21. The isolated nucleic acid of claim 20, wherein said conservative amino acid is selected from the group consisting of threonine-155, glutamine-190, and leucine-226.

22. An isolated influenza A virus hemagglutinin wherein said hemagglutinin comprises a mutation which substantially abrogates binding of said hemagglutinin to a sialic acid containing receptor and further wherein said mutation does not affect the fusogenic capability of said hemagglutinin.

23. A pseudotyped murine leukemia virus (MLV) comprising a mutant influenza A hemagglutinin, wherein said mutant hemagglutinin comprises a first mutation comprising a change from threonine to serine at amino acid 155, and further wherein said mutant hemagglutinin comprises a second mutation comprising a change from leucine to valine at amino acid 226, wherein said pseudotyped MLV expresses said mutant hemagglutinin and wherein said mutant hemagglutinin is in the envelope of said pseudotyped MLV.

24. The pseudotyped MLV of claim 23, wherein said hemagglutinin further comprises a third mutation comprising an amino acid substitution which causes said mutant hemagglutinin to undergo low-pH induced conformational changes to a fusogenic form.

25. The pseudotyped MLV of claim 24, wherein said third mutation comprises an amino acid substitution selected from the group consisting of a substitution from histidine to glutamine at amino acid 17 and a substitution from asparagine to glycine at amino acid 112.

26. A composition comprising a co-pseudotyped enveloped virus expressing a mutant hemagglutinin and a targeting molecule wherein said co-pseudotyped virus binds to a target cell expressing a receptor for said targeting molecule and further wherein said mutant hemagglutinin causes said virus to fuse with said target cell.

27. An isolated mammalian cell comprising the pseudotyped virus of claim 23.

28. An isolated mammalian cell comprising the co-pseudotyped virus of claim 26.

29. A method of targeting delivery of a component to a desired cell, said method comprising inserting a mutant hemagglutinin and a targeting molecule on the surface of a vector, wherein said targeting molecule mediates binding of said vector to a targeting molecule-specific receptor on said cell, and further wherein said mutant hemagglutinin mediates membrane fusion of said vector with the membrane of said cell, thereby delivering said component to said cell.

30. The method of claim 29, wherein said component is selected from the group consisting of a nucleic acid, an antisense nucleic acid, a gene, a protein, a peptide, a Vpr protein, an enzyme, an intracellular antagonist of HIV, a radionuclide, a cytotoxic compound, an antiviral agent, and an imaging agent.

* * * * *

SEQUENCE LISTING

```
<160> NUMBER OF SEQ ID NOS: 17

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence:  PCR
          Primers For Influenza Virus A Strain X-31 Hemagglutinin

<400> SEQUENCE: 1
ttgtccaaat cagg                                                         14

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:  PCR
          Primers For Influenza Virus A Strain X-31 Hemagglutinin
```

```
<400> SEQUENCE: 2
tatctagatc gactaataca c                                              21

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 3
cctgatttgg acaa                                                      14

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 4
aatacgactc actatag                                                   17

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 5
ccagattatg cctcccttag g                                              21

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 6
cttcctgatt tggacaacca gttc                                           24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 7
ctactagaca gaccccttac c                                              21

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin
```

<400> SEQUENCE: 8
gaactggttg tccaaatcag gaag 24

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 9
gttcaagcat cagggagagt cacagtc 27

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 10
gcttattcta ctagacacac cccttaccca g 31

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 11
ctgggtaagg ggtgtgtcta gtagaataag c 31

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 12
tgggaatgct tccatttgga gtgatgc 27

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 13
gcaccgcatg ctgtcccagg c 21

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

```
<400> SEQUENCE: 14
gataaatctg gagcctccaa gggtgggtct cgcgg                                    35

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 15
catttccgag ccagtcaggt c                                                   21

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 16
cttggatcca attcagaggt tcagaactct g                                        31

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: PCR
      Primers For Influenza Virus A Strain X-31 Hemagglutinin

<400> SEQUENCE: 17
tttataccgc gggatctgca ggtcgcagtt ccc                                      33
```